(12) United States Patent
Bernardoni et al.

(10) Patent No.: US 12,268,429 B2
(45) Date of Patent: Apr. 8, 2025

(54) DEVICE FOR TENSIONING A SURGICAL THREAD AND BONE CERCLAGE KIT

(71) Applicant: MEDACTA INTERNATIONAL SA, Castel San Pietro (CH)

(72) Inventors: Massimiliano Bernardoni, Castel San Pietro (CH); Francesco Siccardi, Castel San Pietro (CH); Ermete Rossi, Castel San Pietro (CH)

(73) Assignee: Medacta International SA, Castel San Pietro (CH)

( * ) Notice: Subject to any disclaimer, the term of this patent is extended or adjusted under 35 U.S.C. 154(b) by 379 days.

(21) Appl. No.: 17/996,363

(22) PCT Filed: Apr. 14, 2021

(86) PCT No.: PCT/IB2021/053061
§ 371 (c)(1),
(2) Date: Oct. 17, 2022

(87) PCT Pub. No.: WO2021/209909
PCT Pub. Date: Oct. 21, 2021

(65) Prior Publication Data
US 2023/0218330 A1 Jul. 13, 2023

(30) Foreign Application Priority Data
Apr. 15, 2020 (IT) .................. 102020000007894

(51) Int. Cl.
*A61B 17/88* (2006.01)
*A61B 17/82* (2006.01)
(52) U.S. Cl.
CPC .......... *A61B 17/8869* (2013.01); *A61B 17/82* (2013.01)

(58) Field of Classification Search
CPC ........................ A61B 17/82; A61B 17/8869
See application file for complete search history.

(56) References Cited

U.S. PATENT DOCUMENTS

| 6,752,810 B1 | 6/2004 | Gao et al. |
| 2002/0072753 A1 * | 6/2002 | Cohen ............... A61B 17/8861 606/103 |

(Continued)

FOREIGN PATENT DOCUMENTS

EP 3278741 A1 2/2018

OTHER PUBLICATIONS

International Search Report and Written Opinion issued in PCT/IB2021/053061, mailed Jul. 5, 2021.

*Primary Examiner* — Olivia C Chang
(74) *Attorney, Agent, or Firm* — Meunier Carlin & Curfman LLC (57) ABSTRACT

A device for tensioning a surgical thread comprising: an elongated body having a tip portion adapted to be arranged in contact with a knot of a surgical thread wound about a patient's bone and a maneuvering member connected to the elongated body by a screw and nut mechanism configured to adjust the distance between said elongated body and said maneuvering member, said maneuvering member having respective coupling portions for coupling opposite ends of the surgical thread wound and knotted about the bone. The opposite ends of the surgical thread reversibly constrainable to the respective coupling portions in a use configuration of the device. The distance between the elongated body and the maneuvering member can be increased along a movement axis to tension the opposite ends so as to tighten the surgical thread about the bone. The tip portion has a groove shaped to receive at least partially the knot.

20 Claims, 10 Drawing Sheets

(56) References Cited

U.S. PATENT DOCUMENTS

2011/0112537 A1     5/2011    Bernstein et al.
2013/0184720 A1     7/2013    Aldridge et al.
2018/0185080 A1*   7/2018    Bosshard ........... A61B 17/8861

* cited by examiner

DEVICE FOR TENSIONING A SURGICAL THREAD AND BONE CERCLAGE KIT

TECHNICAL FIELD

The present invention relates to a device for tensioning a surgical thread and a bone cerclage kit comprising such a device.

In particular, the present invention relates to a device for tensioning a surgical thread which can be used in the orthopedic field to carry out operating techniques for the cerclage of fractured bones.

BACKGROUND ART

Cerclage basically consists of winding a surgical thread (or cable) about two or more parts of a patient's fractured bone to hold them together and prevent the separation thereof.

The most common surgical techniques to date include, after having incised the patient at the bone to be operated on, the use of a passer instrument (or even simply referred to as a "passer") for cerclage which allows a surgical thread made of stainless steel to be passed about the fractured bone so as to circumnavigate it.

The passer is then removed, and the two ends of the thread can now be fixed on opposite arms of a special surgical instrument having the function of first tensioning, and then twisting, the two ends of the thread.

The surgeon inserts the aforementioned instrument into the wound, placing it against the bone, and fixes the two ends of the thread at the respective arms of the instrument. At that point, by manually activating appropriate tensioning means, the surgeon pulls the two ends of the thread until they are tensioned according to a given tension.

Now that the ends of the thread are properly tensioned, the surgeon can rotate the instrument about an axis perpendicular to the bone to twist the thread at the bone, so as to fix the thread to the bone, thus creating the so-called cerclage.

In fact, after a few turns of the instrument, the thread wound about the bone remains tightened about the bone, so it is no longer necessary to apply tension to the thread, which is why at this point it is possible to extract the instrument and cut the excess part of the thread.

Although the cutting step allows removing most of the excess thread, it is however necessary to leave a "snag" (i.e., a sharp protrusion) of twisted thread of adequate size in the patient's body, so that the thread does not untie when the cerclage obtained fails.

In fact, since it is not possible to stably fasten a metal surgical thread by obtaining a knot (due to the high surface smoothness of the metal), it is necessary to proceed with the twisting, with the consequent need to leave a fastening snag inside the patient's body.

However, the Applicant has observed how this metal snag protruding from the bone can cause pain, injury, and lacerations in the surrounding soft tissues.

The Applicant has found that the use of a thread made of softer material, instead of metal, could overcome such drawbacks connected to the presence of the snag.

However, a softer thread cannot be twisted about the bone and then remain in place for stable cerclage, but must be knotted.

However, the creation of a cerclage knot would require a larger wound (or the need to widen the wound with obvious negative consequences for the patient) in order to allow the surgeon to pull the two ends of the thread and tighten the loop about the fractured bone. In fact, to obtain an effective tensioning of the thread so as to tighten the knot on the bone, the two ends of the thread must be pulled in opposite and parallel directions, for which a considerable maneuvering space around the bone would be necessary.

The wound which is made in the patient is basically minimal to allow the operation to be carried out as noninvasively as possible; furthermore, the bone is surrounded by soft tissues whereby the maneuvering space is very limited. Therefore, an effective thread tensioning according to this technique is neither advisable nor easily practicable.

Object of the Invention

In this context, it is the technical task underlying the present invention to suggest a device for tensioning a surgical thread and a bone cerclage kit which overcome one or more of the drawbacks of the prior art mentioned above.

In particular, it is an object of the present invention to provide a device for tensioning a surgical thread which is small in size and which allows tensioning a surgical thread wound about a patient's bone in the smallest possible space in a practical and effective manner.

It is a further object of the present invention to suggest a bone cerclage kit which allows obtaining a reliable, minimally invasive cerclage which protects the patient's health (in particular the integrity of the soft tissues surrounding the bone).

The technical task and the specified objects are substantially achieved by a device for tensioning a surgical thread comprising the technical features set forth in one or more of the appended claims.

In particular, the present invention provides a device for tensioning a surgical thread comprising an elongated body and a maneuvering member.

The elongated body extends along a longitudinal axis and has a tip portion adapted to be arranged in contact with a knot of a surgical thread wound about a patient's bone.

The maneuvering member is connected to the elongated body and is adapted to be arranged outside the patient's body.

In particular, the elongated body is connected to the maneuvering member by means of a screw and nut-screw mechanism configured to mutually space apart or approach the elongated body and the maneuvering member.

The elongated body has respective coupling portions configured to couple opposite ends of the surgical thread wound and knotted about the bone. The opposite ends of the surgical thread can be reversibly constrained to the respective coupling portions in a use configuration of the device.

The elongated body and the maneuvering member can be mutually spaced apart along a movement axis coinciding with the longitudinal axis of the elongated body in order to tension the opposite ends of the surgical thread so as to tighten the surgical thread about the bone.

In other words, by spacing the elongated body apart from the maneuvering member, the two opposite ends of the thread are pulled, thus tightening the knot.

Advantageously, the tip portion has a groove shaped to receive at least partially the knot in the use configuration of the device.

The groove extends perpendicular to the movement direction to open on opposite sides of a sidewall of the elongated body at respective return portions along which the opposite ends of the surgical thread can be returned toward the coupling portions.

In other words, the groove defines a through indent of the tip portion adapted to face the bone in the use configuration of the device.

Advantageously, the opposite ends of the surgical thread can thus be arranged tangentially to the bone over a first stretch between the return portions inside the groove, and transversely to said bone along respective second stretches, having a greater length than the first stretch, between the return portions and the coupling portions.

Therefore, by virtue of the device of the present invention, by pulling the two ends of the thread along the second stretches (transversal to the bone surface), it is possible to effectively tighten the knot arranged in the groove about the bone, since inside the first stretch (connected at the second stretches) the two ends of the thread are tensioned along opposite and parallel directions.

Therefore, the traction exerted on the knot by the ends of the thread pulled in the first stretch of small size is very effective due to the favorable distribution of the applied forces; such a traction is returned in the second stretches to advantageously operate in a small volume.

Therefore, the presence of a first stretch tangential to the bone allows an efficient tensioning of the thread which is transferred to the second stretches in the smallest possible space.

In other words, by virtue of the device of the present invention, it is therefore possible to pull the surgical thread horizontally (in a small stretch) while applying a vertical traction (along stretches of large dimension) in the smallest possible space.

The presence of the groove on the tip portion allows tightening the knot effectively.

Furthermore, by virtue of the present device it is possible to carry out a cerclage starting from a knot obtained by winding the surgical thread about the bone to be operated on.

In fact, instead of twisting the thread, by operating on a knot it is possible to make the cerclage more effective by reducing the risk of untying and to allow the use of a thread made of soft material which can prevent tearing the surrounding soft tissues during and after the operating steps.

According to a further aspect of the present invention, a bone cerclage kit is also provided, comprising a surgical thread made of biocompatible fabric configured to be wound about a patient's bone to obtain a knot, and a device for tensioning said surgical thread in accordance with the present invention.

Advantageously, the groove of the tip portion is configured to be arranged in contact with the knot in the use configuration of the device.

The thread in biocompatible fabric is a soft thread which has many advantages, including the possibility of not damaging the bone and surrounding tissues.

By virtue of the use of a surgical thread made of biocompatible fabric and the tensioning device according to the present invention, it is therefore possible to achieve an effective cerclage of the bone using a knot, which is much more reliable than a twisted thread.

Once the knot has been tightened about the bone, it is possible to use simple surgical scissors to remove the excess thread from the two ends, leaving only a small knot in sight, which being made of fabric will prevent injuries and lacerations of the surrounding tissues.

Surgical scissors are also less bulky and much more maneuverable than surgical forceps, therefore the operation of cutting and removing the excess thread is practical and efficient by virtue of the present invention.

Therefore, the presence of a knot allows a safer and more stable cerclage which does not require a bulky and dangerous "snag."

The kit of the present invention allows operating in a minimally invasive manner, achieving an efficient cerclage.

The dependent claims, incorporated by reference herein, correspond to different embodiments of the invention.

BRIEF DESCRIPTION OF THE DRAWINGS

Further features and advantages of the present invention will become more apparent from the following indicative and thus non-limiting description of a preferred, but not exclusive, embodiment of a device for tensioning a surgical thread and a bone cerclage kit, as shown in the accompanying drawings, in which.

DETAILED DESCRIPTION OF PREFERRED EMBODIMENTS OF THE INVENTION

With reference to the accompanying drawings, reference numeral 1 indicates as a whole a device for tensioning a surgical thread, hereinafter simply device 1.

The device 1 comprises an elongated body 10 and a maneuvering member 20.

Figure 4:
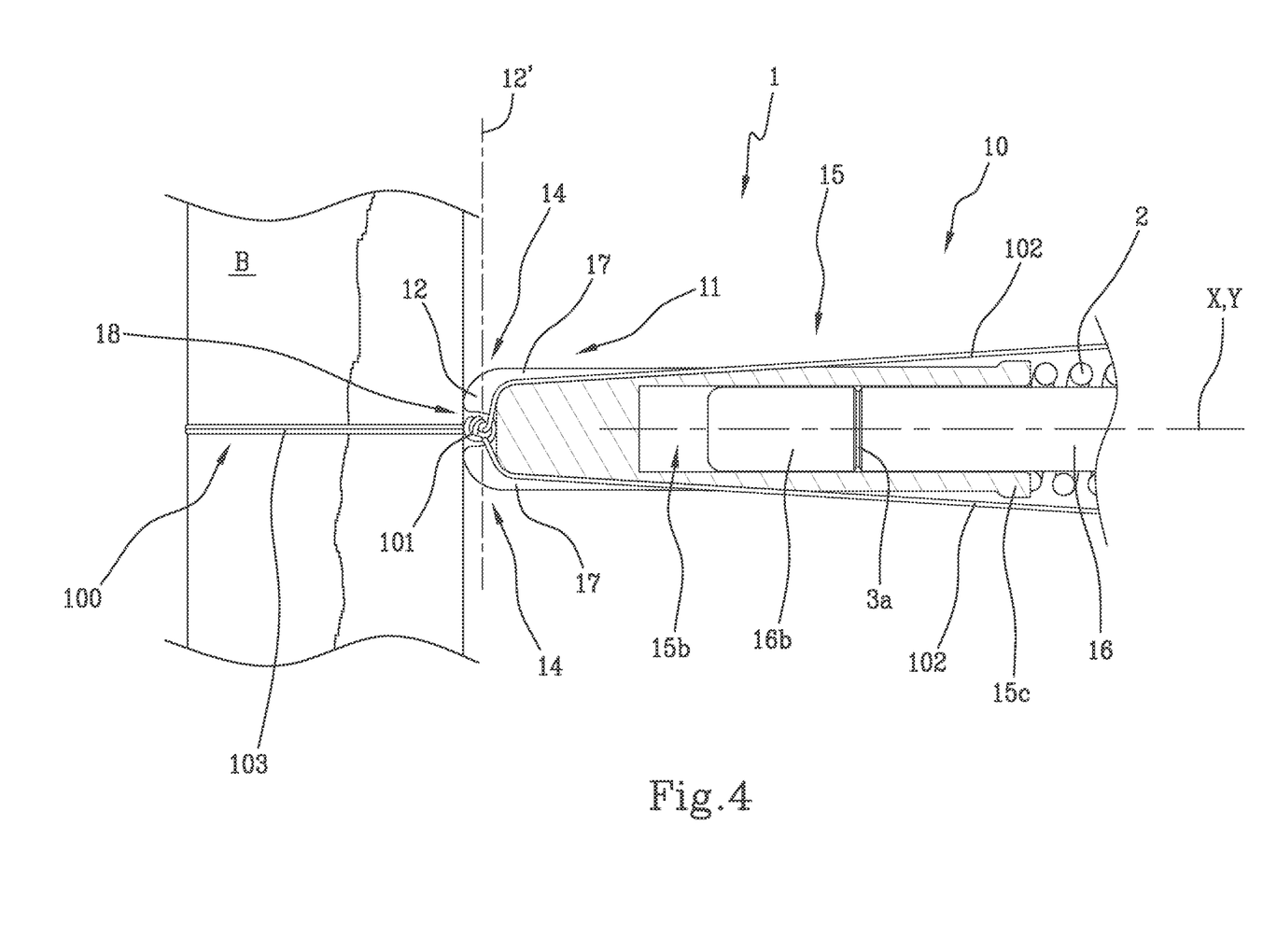
FIG. 4 is a sectional side view of a bone and of the device in FIG. 3.

The elongated body 10 extends along a longitudinal axis Y and has a tip portion 11 adapted to be arranged in contact with a knot 101 of a surgical thread 100 wound about a patient's bone B, for example a damaged bone B (such as diagrammatically shown in FIG. 4).

Preferably the knot 101 is obtained in contact with the bone B, i.e., the thread 100 is knotted so that the knot 101 is arranged in contact with the surface of the bone B.

The maneuvering member 20 is connected to the elongated body 10 and is adapted to be arranged outside the patient's body when using the device 1 (i.e., outside the wound) and has respective coupling portions 21 for coupling opposite ends 102 of the surgical thread 100 wound and knotted about the bone B.

The opposite ends 102 of the surgical thread 100 can be reversibly constrained to the respective coupling portions 21 in a use configuration of the device 1.

In particular, the elongated body 10 and the maneuvering member 20 can be mutually spaced apart along a movement axis X coinciding with the longitudinal axis Y in order to tension the opposite ends 102 of the surgical thread 100 so as to tighten the surgical thread 100 about the bone B.

In other words, in the use configuration of the device 1, by spacing apart the elongated body 10 (the tip portion 11 of which is arranged in contact with the knot 101) and the maneuvering member (to which the opposite ends 102 of the thread 100 is fastened at the respective coupling portions 21) along the movement axis X, it is possible to tension the opposite ends 102 causing the knot 101 to approach the bone B and a consequent tightening of the knot 101.

Advantageously, the tip portion 11 has a groove 12 shaped to receive at least partially the knot 101 in the use configuration of the device 1.

The groove 12 extends perpendicularly to the movement axis X along an extension direction 12' to open on opposite sides of a sidewall 13 of the elongated body 10 at respective return portions 14, along which the opposite ends 102 of the surgical thread 100 can be returned toward the coupling portions 21.

Thereby, the opposite ends 102 of the surgical thread 100 can be arranged tangentially to the bone B over a first stretch (clearly visible in FIG. 4) between the return portions 14 inside the groove 12, and transversely to the bone B along respective second portions, having a greater length than the first stretch, between the return portions 14 and the coupling portions 21.

According to the present invention, the elongated body 10 is connected to the maneuvering member 20 by means of a screw and nut-screw mechanism 30 configured to mutually space apart or approach the elongated body 10 and the maneuvering member 20.

Advantageously, the use of a screw and nut-screw mechanism 30 allows precisely adjusting the mutual distance between the two elements to obtain a progressive tensioning of the opposite ends 102 of the thread 100, as will become apparent in the following description.

Preferably, the maneuvering member 20 comprises a knob 22 which can be rotated about the movement axis X to screw or unscrew the screw and nut-screw mechanism 30, and a sleeve 23 on which the two coupling portions 21 are obtained.

Figure 1:
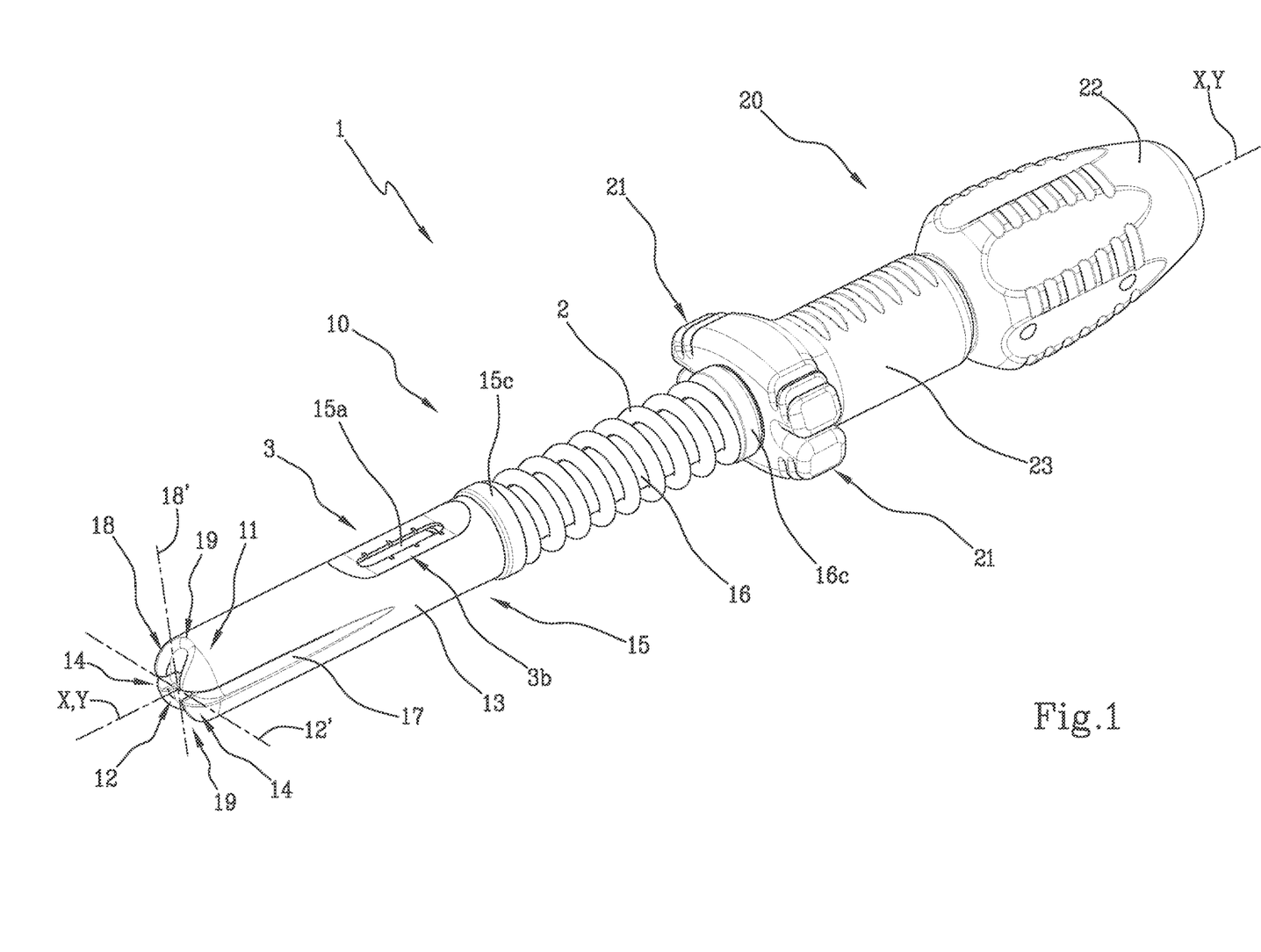
FIG. 1 is a diagrammatic perspective view of a device for tensioning a surgical thread according to the present invention.
Figure 2:
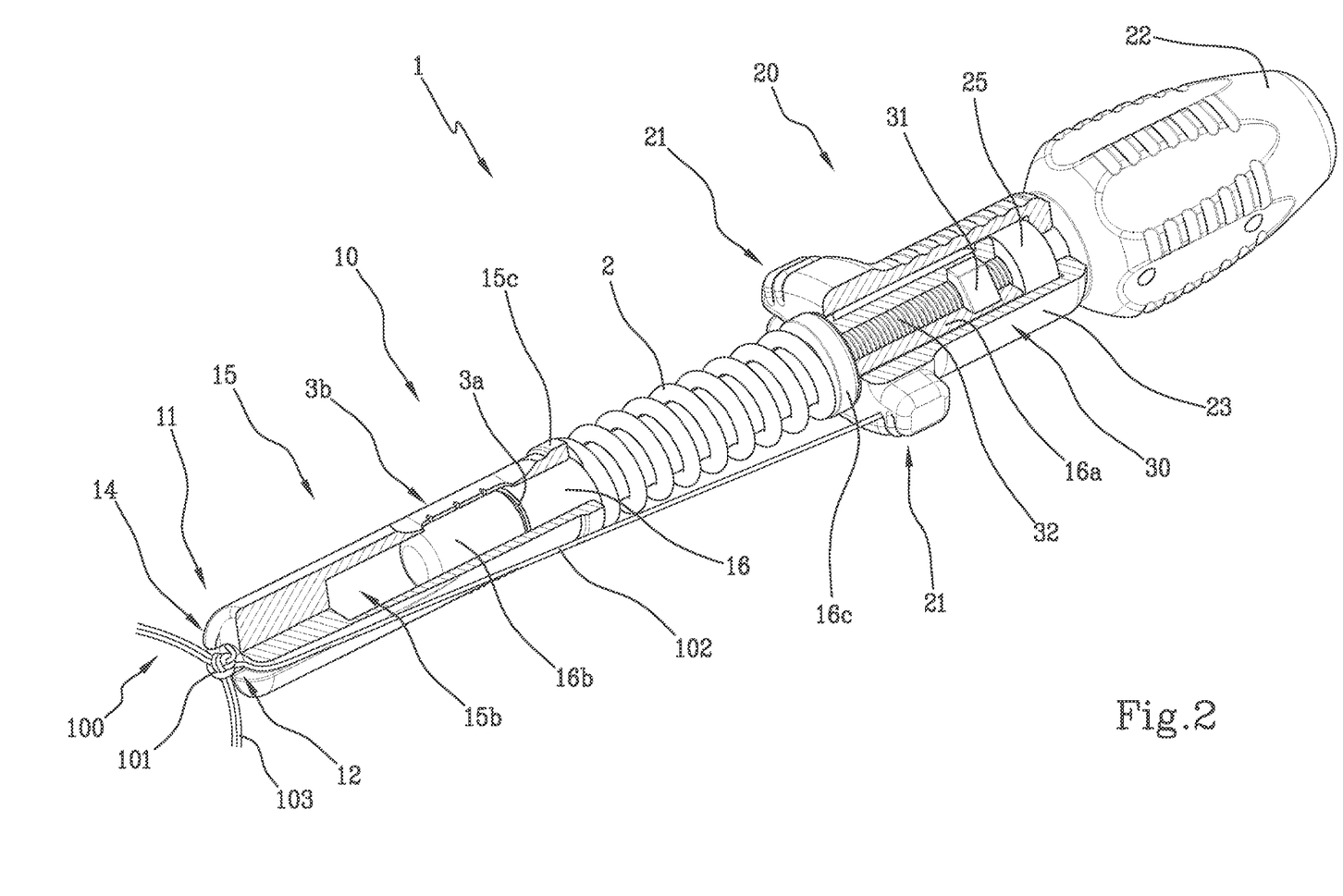
FIG. 2 is a partially exploded diagrammatic perspective view of the device in FIG. 1 during a first use configuration of the device.
Figure 3:
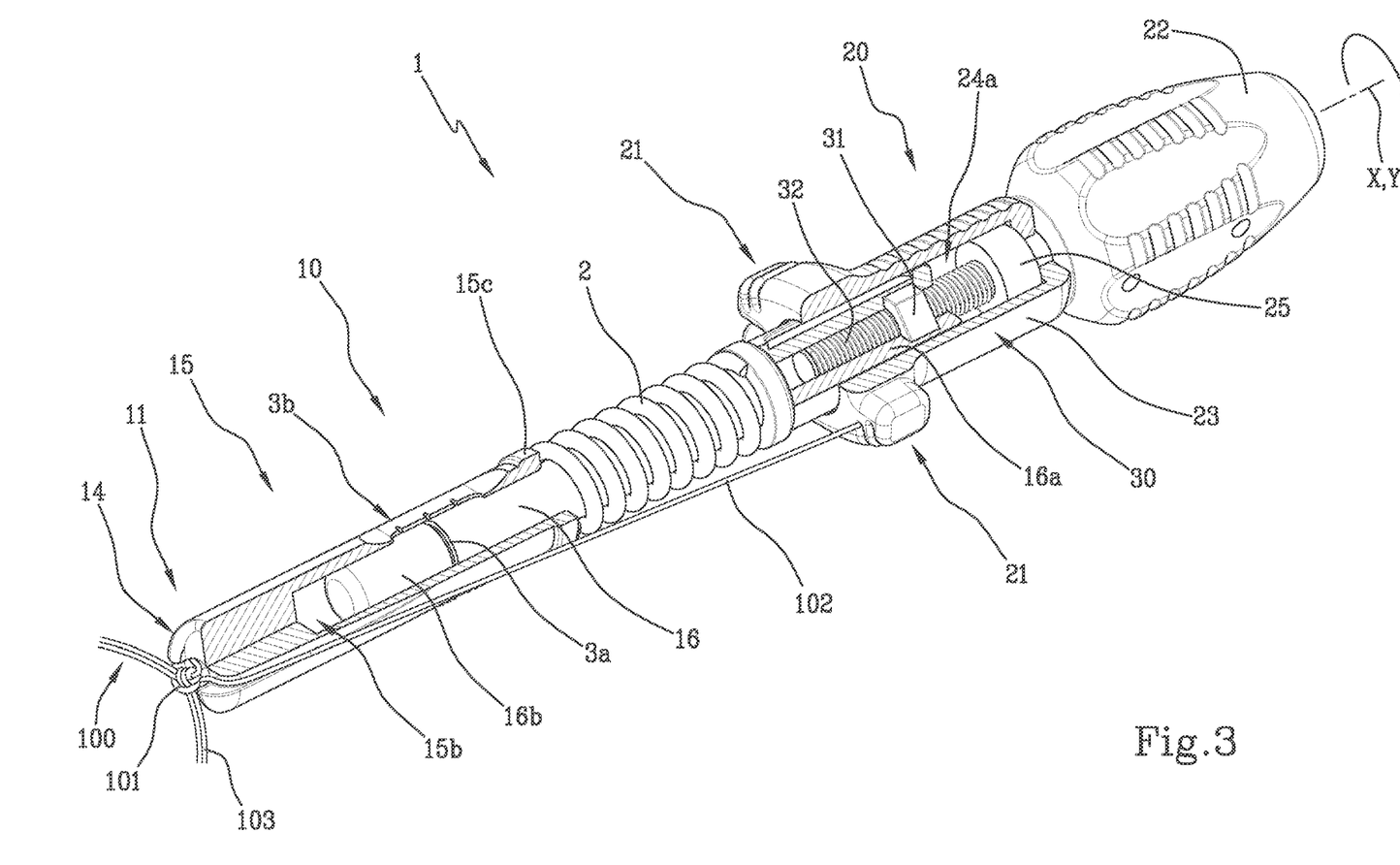
FIG. 3 is a partially exploded diagrammatic perspective view of the device in FIG. 1 during a second use configuration of the device.

In particular, with reference to the embodiment shown in FIGS. 1-3, the two coupling portions 21 are obtained on opposite sides of the sleeve 23 with respect to a direction parallel to the extension direction 12' of the groove 12.

Advantageously, the knob 22 is rotationally connected to the sleeve 23.

Even more preferably, the elongated body 10 and the sleeve 23 are mutually translatable along the movement axis X and rotationally fixed about the movement axis X.

In other words, the elongated body 10 and the sleeve 23 can be mutually spaced apart and approached along the movement axis X but they cannot be rotated with each other, therefore the coupling portions 21 are fixed with respect to the rotation of the knob 22 of the maneuvering member 20.

Preferably, the elongated body 10 comprises a head element 15 on which the tip portion 11 is obtained, and a stem 16 extending along the longitudinal axis Y and operatively interposed between the head element 15 and the maneuvering member 16.

In other words, the head element 15 and the knob 22 are arranged on opposite sides along the movement axis X of the device 1.

Preferably, the stem 16 has a first end 16a inserted inside a respective recess 24a of the maneuvering member 20 and a second end 16b, opposite the first end 16a, inserted in a respective recess 15b of the head element 15, axially opposite to said tip portion 11.

In other words, the head element 15 has a recess 15b extending along the longitudinal axis Y and open on the axially opposite side of the head element 15 with respect to the tip portion 11; likewise, the sleeve 23 has a recess 24a extending along a direction coinciding with the movement axis X and open on the axially opposite side of the sleeve 23 to the knob 22.

Advantageously, therefore, the stem 16 can be moved between the respective recesses 24a, 15b to obtain the mutual spacing apart of the elongated body 10 and the maneuvering member 20.

Preferably, moreover, with reference to the embodiment shown in FIGS. 1-3, the screw and nut-screw mechanism 30 comprises a nut-screw 31, fixed to the first end 16a of the stem 16, and a screw 32, arranged along the movement axis X and fixed inside the respective recess 24a of the maneuvering member 20.

In particular, the screw 32 is reversibly screwable on the nut-screw 31 to allow the translation of the stem 16 so as to obtain the mutual spacing apart or approaching of the maneuvering member 20 and the elongated body 10.

Furthermore, the sleeve 23 is preferably coupled to the knob 22 by means of a dowel 25 arranged inside the recess 24a.

Preferably the device 1 comprises a spring 2 operatively interposed between a flange 16c of said stem 16 and a shoulder 15c defined by an outer edge of said head element 15.

The spring 2 is advantageously configured to oppose the advancement of the stem 16 inside the respective recess 15b of the head element 15 toward the tip portion 11.

In other words, the spring 2 is configured to oppose the mutual spacing apart between the elongated body 10 and the maneuvering member 20, and in particular the unscrewing of the nut-screw 31 from the screw 32 with reference to FIGS. 1-3.

Furthermore, the device 1 preferably comprises a system 3 for detecting and indicating the tension value to which the thread 100 is subjected in the use configuration of the device 1. Advantageously, by virtue of the system 3, the surgeon can therefore monitor whether the tension applied to the thread 100 is adequate in real time.

Even more preferably the head element 15 has a window 15a through which a portion of stem 16 inserted in the respective recess 15b of the head element 15 is visible. The detection and indication system 3 further comprises indicators 3a, 3b obtained on the stem 16 (a notch in the embodiment in FIG. 1, or a pin in the embodiments in FIGS. 5 and 10) and on the window 15a (for example a graduated scale with the indication of the tension expressed in Newtons of the force applied in the embodiments in FIGS. 5 and 10, or a series of notches in the embodiment in FIG. 1), respectively, and representative of a tension value of the spring 2 and/or of an insertion depth value of the stem 16 in the recess 15b of the head element 15.

Advantageously, therefore, the surgeon can have rapid feedback of the tension value of the thread 100 in order to compare the values detected by the indicators 3a, 3b with predetermined reference values.

For example, the optimal thread tension which the surgeon can achieve with the device 1 is 400 N.

According to the present invention, moreover, the sidewall 13 of the elongated body 10 preferably has two slots 17, each slot 17 departing from a respective return portion 14 along a respective extension direction directed toward a respective coupling portion 21, so that the groove 12 and the two slots 17 define a single "U"-shaped groove of the elongated body 10.

Advantageously, the slots 17 allow a housing guide to be obtained for the opposite ends of the thread 102 directed toward the coupling portions 21, so that in the use configuration of the device 1 they do not slip off the tip portion 11.

Preferably, with reference to the embodiment in FIG. 1, the extension directions of the slots 17 are parallel to the movement axis X.

Preferably the return portions 14 define rounded connecting edges between the groove 12 and the two slots 17 so as to avoid the onset of localized tensions at any edges.

Preferably, the tip portion 11 further has a secondary groove 18 extending transversely, preferably perpendicularly, to the groove 12 along a respective extension direction 18'.

The secondary groove 18 is advantageously shaped so as to receive at least partially the knot 101 at an intersection point, not visible in the accompanying drawings, with the groove 12.

Advantageously, moreover, the secondary groove 18 extends perpendicularly to the movement axis X to open on opposite sides of the sidewall 13 of the elongated body 10 at two openings 19 for the passage of the part 103 of thread 100 wound about the bone B.

Preferably, the two openings 19 are angularly spaced by 90° with respect to the return portions 14 with respect to the intersection point between the two grooves 12, 18.

In other words, the secondary groove 18 is also adapted to receive the knot 101 at least partially and to house the part 103 of thread 100 wound about the bone B, so that the opposite ends 102 of the thread 100 are arranged inside said groove 102 perpendicular to said part 103.

Figure 5:
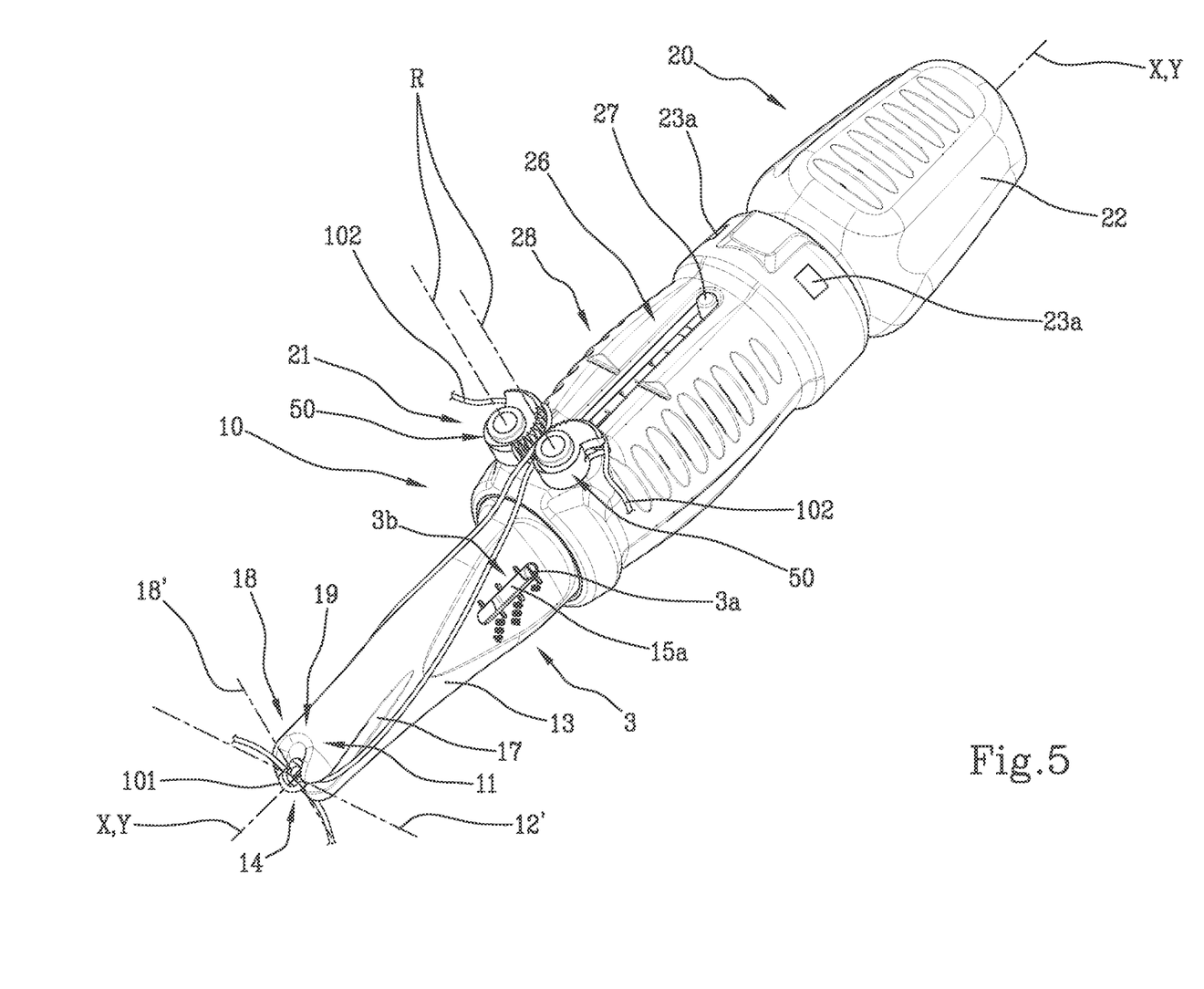
FIG. 5 is a diagrammatic perspective view of a first alternative embodiment of the device in FIG. 1.
Figure 10:
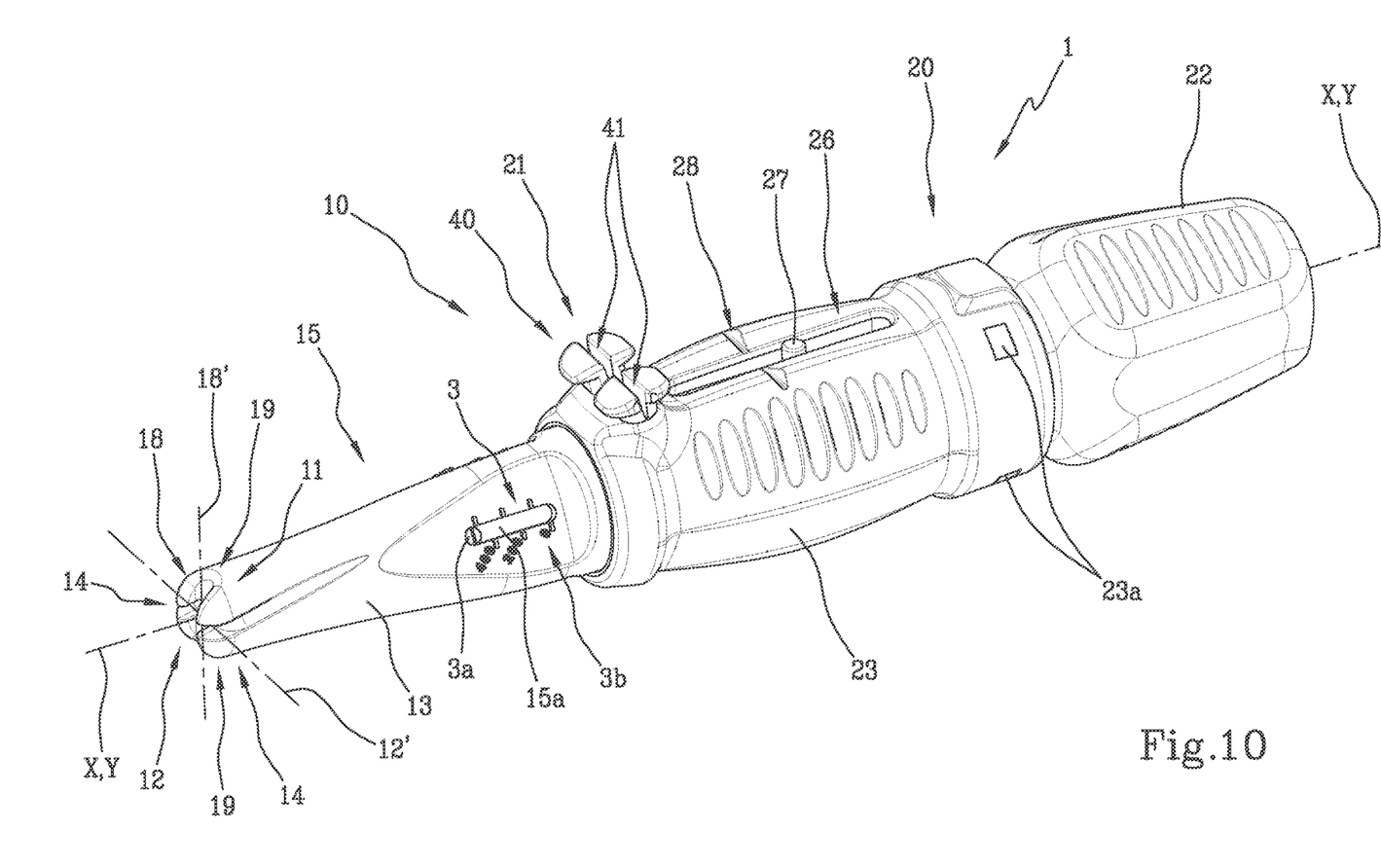
FIG. 10 is a diagrammatic perspective view of a second alternative embodiment of the device in FIG. 1.

FIGS. 5 and 10 refer to two alternative embodiments of the present invention in which the screw and nut-screw mechanism 30 is obtained differently than that of the device in FIG. 1. Preferably, in fact, as clearly seen in FIGS. 6, 7 and 8, the knob 22 has an inner threaded portion 22a and the first end 16a of the stem 16 is threaded to be reversibly screwed inside the inner threaded portion 22a to allow the translation of the stem 16 so as to obtain the mutual spacing apart or approaching of the maneuvering member 20 and the elongated body 10.

Advantageously, the first threaded end 16a and the inner threaded portion 22a define the screw and nut-screw mechanism 30, in which in particular the first threaded end 16a functions as a "screw" while the inner threaded portion 22a functions as a "nut-screw".

In other words, by unscrewing the knob 22 the first end 16a of the stem 16 will be moved in extraction from the respective recess 24a of the maneuvering member 20, in particular in this case the recess 24a is obtained in the knob 22.

Preferably, the knob 22 is rotationally connected to the sleeve 23 at two anti-extraction blocks 23a.

The spring 2 is preferably arranged inside the sleeve 23. Advantageously, it is thus possible to prevent pinching and accidental contacts with surrounding tissues during the operation on the patient's bone.

Preferably, moreover, the maneuvering member 20, and even more preferably the sleeve 23, comprises an inspection eyelet 26 through which the stem 16 is visible and in which the stem 16 comprises a pin 27 which is movable inside the inspection eyelet 26 upon the actuation of the screw and nut-screw mechanism 30. In particular, the inspection eyelet 26 is associated with visual elements 28 representative of the advancement of the stem 16.

Advantageously, therefore, the pin 27 allows the surgeon to see how much the stem 16 is moving.

With reference to the first alternative embodiment shown in FIGS. 5, 6, 7, 7A, 8, 8A, preferably the coupling portions 21 comprise two jaws 50 which are rotatable about respective parallel rotation axes R to retain the opposite ends 102 of the surgical thread 100.

Figure 9:
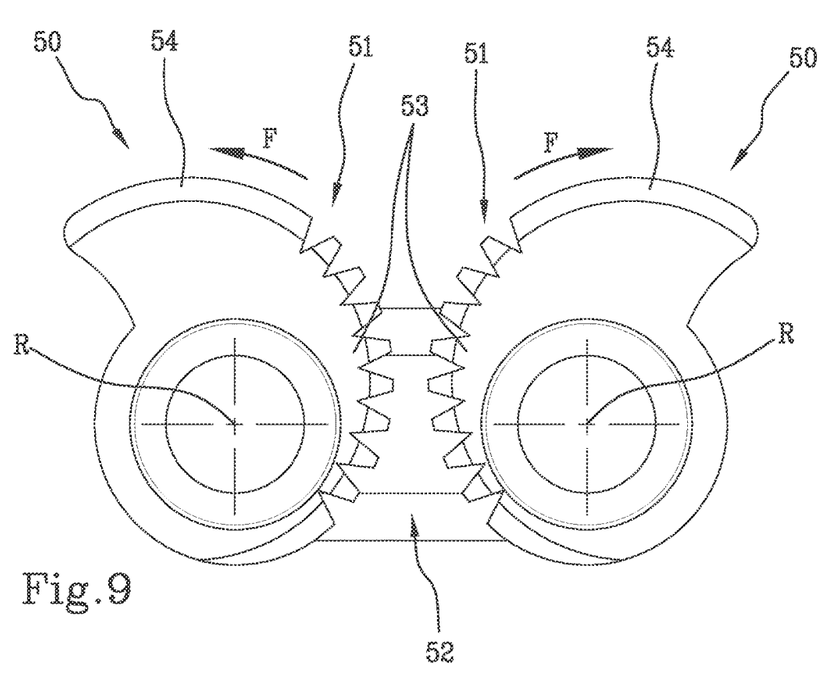
FIG. 9 is a front view of the jaws of the device in FIG. 5, and FIGS. 9A, 9B are a sectional and a side view of a jaw in FIG. 9, respectively.
Figure 9A:
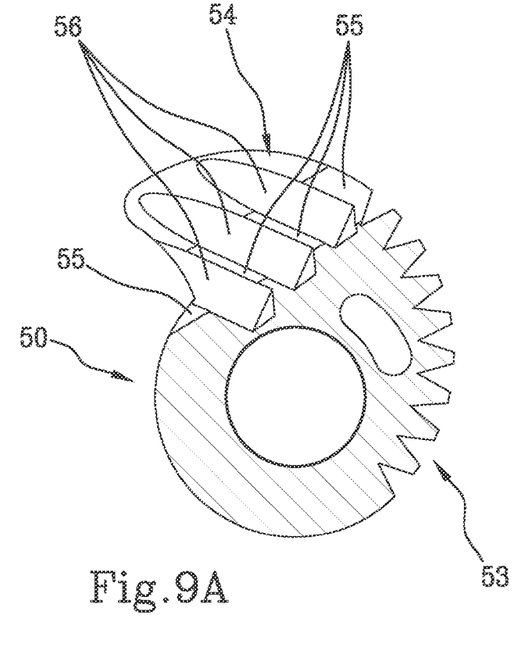
Figure 9B:
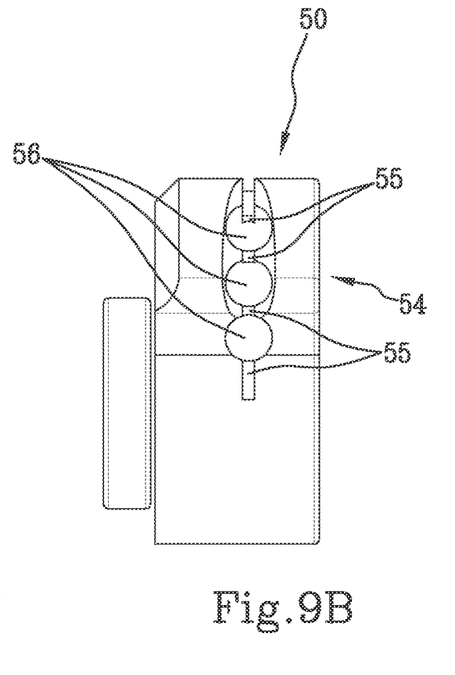

As clearly seen in FIGS. 9, 9A and 9B, in particular the jaws 50 have respective peripheral portions 51 with increasing diameter facing each other to define a throat 52 of variable thickness adapted to receive the opposite ends 102 under insertion.

The coupling portions 21 further comprise two torsional springs, not shown, associated with the respective jaws 50 and configured to progressively oppose the discordant rotation of the jaws 50 which causes an increase in the thickness of the throat 52.

Advantageously, therefore, the opposite ends 102 of the thread 100 can be inserted side by side inside the throat 52 by forcing the two jaws 50 to "open" against the force of the torsional springs, i.e., to rotate in the direction indicated by the arrows F1 in FIG. 9 so that the thickness of the throat 52 increases, allowing the insertion of the opposite ends of the thread 100. At the end of the traction due to the insertion of the two opposite ends 102 between the jaws 50, the two peripheral portions 51 will rotate in the opposite direction with respect to the arrows F1 under the return force of the torsional springs to "close" the jaws 50, i.e., to decrease the thickness of the throat 52 until the two opposite ends 102 remain crushed and retained trapped in the peripheral portions 51.

In other words, the jaws 50 are shaped like cams and the coupling portions 21 substantially define a cam-cleat mechanism.

Advantageously, the cam-cleat mechanism thus defined prevents the thread 100 from slipping out of the jaws 50 in the opposite direction to that of insertion and ensures an excellent coupling and retaining element of the cable for tensioning the opposite ends 102.

The coupling portions 21 thus formed are configured as a practical and efficient tool for tensioning the thread 100.

With particular reference to FIGS. 9, 9A and 9B, preferably each peripheral portion 51 has a first part 53 defining the throat 52 and a second part 54 having a series of retaining indents 55, preferably of constant thickness, obtained transversely to the rotation axes R of the jaws 50 between which open return and positioning recesses 56 of the opposite ends 102 of the thread 100 are interposed.

Preferably, the first part 53 has a toothed profile, so as to improve the retaining capacity of the thread 100.

Advantageously, the opposite ends 102 can be inserted, upon the application by the surgeon of a certain traction force, in sequence inside the open return and positioning recesses 56 passing through respective retaining indents 55, so as to direct the ends 102 towards predetermined directions.

Preferably, the thickness of the retaining indents 56 is less than or equal to the diameter of the thread 100.

Advantageously, the surgeon, after having arranged the tip portion 11 of the elongated body 10 against the knot 101, can proceed with the insertion of the opposite ends 102 inside the throat 52 (FIG. 5).

Figure 6:
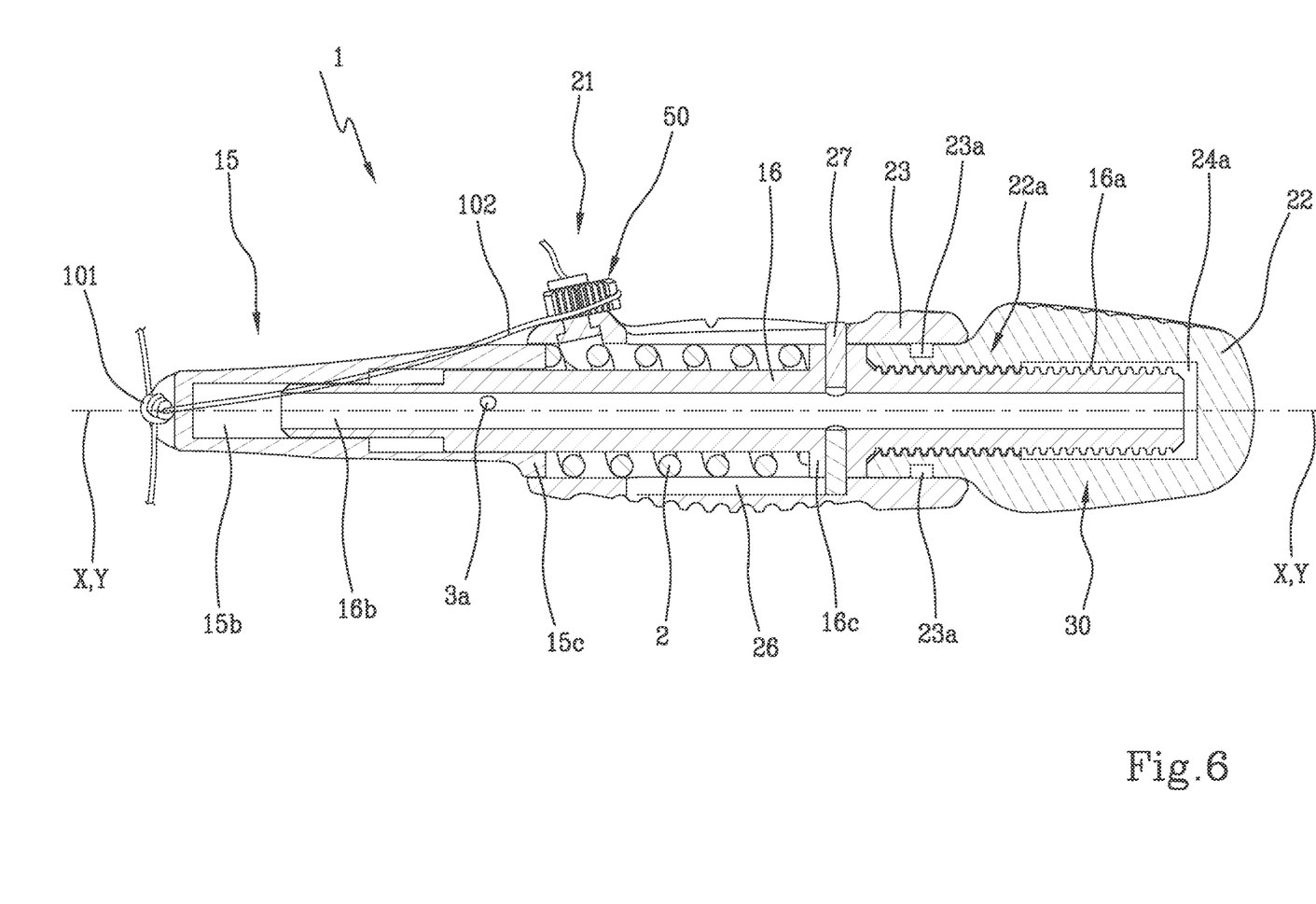
FIG. 6 is a diagrammatic sectional view of the device in FIG. 5 during an inoperative configuration.

FIGS. 5 and 6 show an operating configuration of the device 1 in which the thread 100 beyond the knot 101 is slack, so that the two opposite ends 102 are not under tension but slack, the spring 2 is at rest, the knob 22 is completely screwed on the first end 16a. In this configuration, the pin 27 is arranged at the beginning of the inspection eyelet 26 and the pin 3a is arranged at the beginning of the window 15a, at the indicator 3b which marks "0".

In other words, the stem 16 has not yet moved and the tension detected by the detection and indication system is equal to 0 (i.e., the opposite ends 102 are not tensioned).

Figure 7:
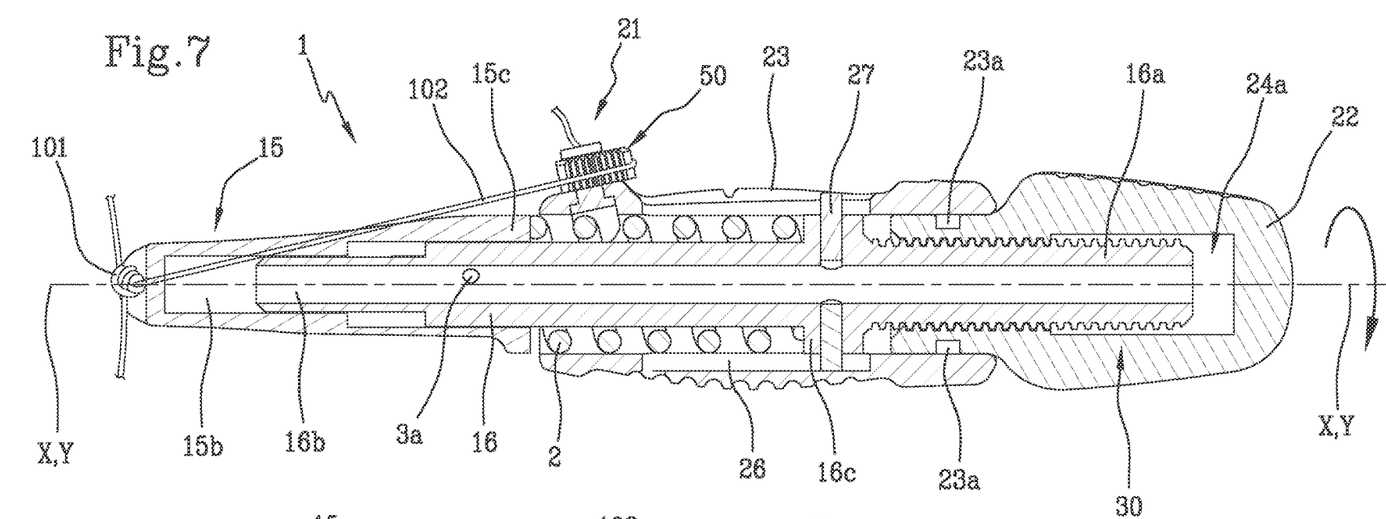
FIG. 7 is a diagrammatic section of the device in FIG. 5 during a first operating configuration.

Upon the unscrewing of the knob 22, for example upon a rotation of two turns of the knob 22 (as shown in FIG. 7), the first end 16a is unscrewed from the threaded portion 22a of the knob 22 causing a compression of the spring 2 and a progressive removal of the head element 15 from the sleeve 23 which allows the opposite ends 102 of the thread 100 to be progressively tensioned (therefore the opposite ends 102 in this situation are no longer slack). Simultaneously with the advancement of the stem 16, the pin 27 advances inside the inspection eyelet 26 to indicate to the surgeon the extent of the removal of the stem 16 from the first recess 24a. In particular, with reference to FIG. 7A, a configuration is shown in which the pin 3a is arranged at the beginning of the window 15a, i.e., at the indicator 3b which marks "0".

Figure 7A:
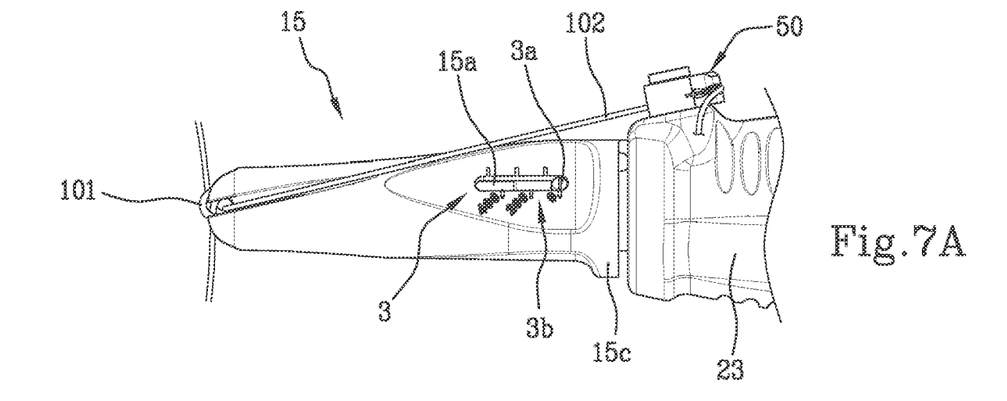
FIG. 7A is a detailed diagrammatic side view of the device in FIG. 5 during the first operating configuration.
Figure 8:
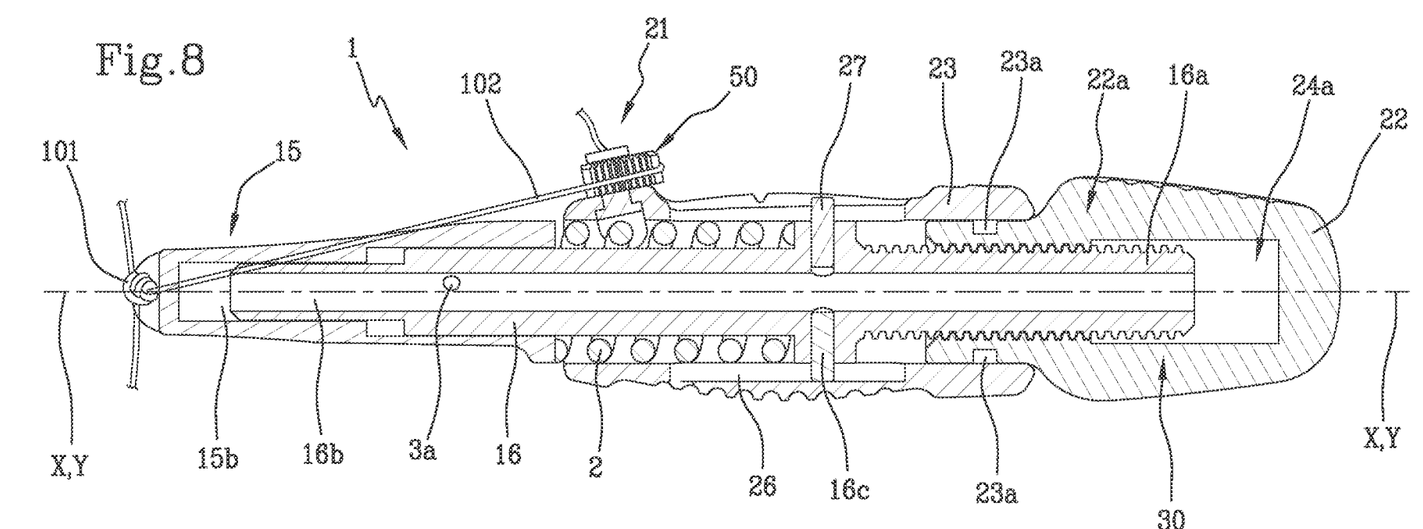
FIG. 8 is a diagrammatic section of the device in FIG. 5 during a second operating configuration.
Figure 8A:
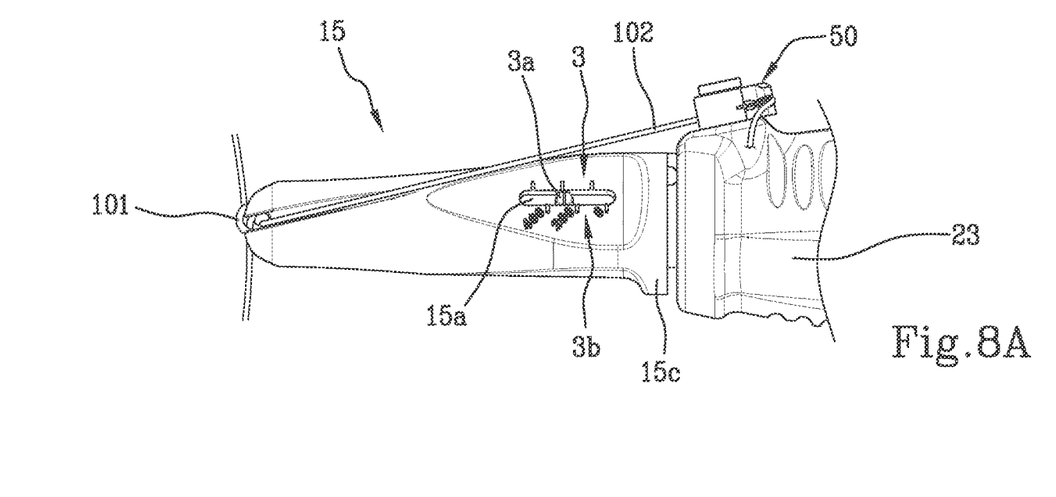
FIG. 8A is a detailed diagrammatic side view of the device in FIG. 5 during the second operating configuration.

In other words, the stem 16 has been moved spaced apart but the tension detected by the detection and indication system is still equal to 0 (i.e., the opposite ends 102 are not tensioned), this is because the opposite ends 102 are no longer slack but are still not tensioned.

Advantageously, the visual elements 28 can be in the form of notches to indicate to the surgeon the limit position of the pin 27 beyond which, according to the appropriate sizing of the device 1, it will no longer be possible to achieve the predetermined target tension value (for example 400N) of the thread 100, if the pin 3a, when the pin 27 has passed such notches, has not yet moved from the indicator 3b which marks "0".

In other words, if the opposite ends 102 have not been correctly coupled and "pre-tensioned" in the jaws 50 (i.e., left too slack), unscrewing the entire knob 22 will not allow achieving the target value; however, by virtue of the presence of the pin 27 and of the visual elements 28, this scenario can be easily overcome by operating a further insertion of the thread 100 in the jaws 50 before continuing with the unscrewing of the knob 22.

If the surgeon, from the configuration illustrated in FIGS. 7 and 7A, proceeds to further unscrew the knob 22, the spring 2 compresses further and the stem 16 advances further in extraction from the knob 22 so that the second end 16b of the stem advances in the respective recess 15b of the head element 15, causing the progressive tensioning of the opposite ends 102.

In this configuration, the pin 27 is further advanced in the inspection eyelet 26 and the pin 3a is advanced inside the window 15a (FIG. 8A), indicating the tension value of the opposite ends 102 obtained to the surgeon.

With reference to the second alternative embodiment of the device 1, shown in FIG. 10, preferably the coupling portions 21 comprise two bitt-like elements 40 having a through anchoring slot 41, preferably of variable thickness, obtained transversely to the movement direction X.

Advantageously, the opposite ends 102 can be wound at least once about the two bitt-like elements 40 and subsequently inserted inside the through anchoring slot 41 until reaching a depth which obtains the retention of the thread 100 by interference.

According to a further aspect of the present invention, a kit for the cerclage of a bone B is further provided, comprising a surgical thread 100 in biocompatible fabric, possibly bioabsorbable, configured to be wound about the bone B to obtain the knot 101 and a device 1 for tensioning said surgical thread 100 as previously described, so that the groove 12 is configured to be arranged in contact with said knot 101 in the use configuration of the device 1.

Operatively, therefore, the surgeon who intends to carry out a cerclage of bone B using the kit provided by the present invention, initially winds the thread 100 about the fractured bone B, obtaining the knot 101.

The surgeon then places the tip portion 11 of the elongated body 10 against the knot 101 so that the knot 101 is at least partially inserted inside the groove 12. Preferably, the part 103 of thread 100 wound about the bone B is partially arranged inside the secondary groove 18.

The two opposite ends 102 of the thread 100 are fastened to the coupling portions 21, preferably passing through the two slots 17.

At this point the surgeon can mutually space apart the elongated body 10 from the maneuvering member 20 to tighten the knot by pulling the ends so as to tighten the knot 101. In other words, a narrowing of the knot 101 is obtained, i.e., a decrease in the part 103 of the thread 100 which is tightened about the bone B.

Preferably, such an operation occurs by turning the knob 22 so as to unscrew the nut-screw 31 from the screw 32 (for the embodiment in FIG. 1) or unscrew the inner threaded portion 22a from the first threaded end 16a of the stem 16 (for the embodiments in FIGS. 5 and 10, causing the partial extraction of the stem 16 from the recess 24a of the maneuvering member 20 and the corresponding advancement of the stem 16 inside the respective recess 15b of the head element 15 of the elongated body 10.

Advantageously, the knot 101 is obtained so as to be irreversibly loosened, so that it is only possible to tighten it.

After having adequately tightened the thread 100 about the bone B, preferably with the support of the detection and indication system 3, it is possible to remove the device 1 from the patient's body.

Such an operation can preferably be obtained by bringing the elongated body 10 closer to the maneuvering member 20 to release the tension in the opposite ends 102 and subsequently releasing the opposite ends 102 from the coupling portions 21.

Finally, the surgeon extracts the device 1 from the patient's body and can proceed with cutting the opposite ends 102 of the thread 100 at the knot 101, on the opposite side with respect to the part 103 wound about the bone B.

The present invention achieves the suggested purposes, overcoming the drawbacks lamented in the prior art and providing the user with a device for tensioning a surgical thread and a bone cerclage kit comprising such a device which allow improving the operating conditions and obtaining an effective cerclage operation.

The invention claimed is:

1. A device for tensioning a surgical thread comprising:
an elongated body extending along a longitudinal axis, the elongated body having a tip portion adapted to contact a knot of a surgical thread wound about a patient's bone; and a maneuvering member connected to said elongated body, said maneuvering member adapted to be arranged outside the patient's body and having respective coupling portions for coupling opposite ends of said surgical thread wound and knotted about said bone, said opposite ends of the surgical thread being reversibly constrainable to said respective coupling portions in a use configuration of the device;

wherein said elongated body is connected to said maneuvering member by means of a screw and nut mechanism configured to adjust the distance between said elongated body and said maneuvering member;

wherein a distance between said elongated body and said maneuvering member can be increased along a movement axis coinciding with the longitudinal axis; to tension the opposite ends of the surgical thread so as to tighten the surgical thread about the bone;

wherein said tip portion has a groove shaped to at least partially receive said knot in the use configuration of the device, said groove extending perpendicularly to the movement axis and opening on opposite sides of a sidewall of said elongated body to define respective return portions along which the opposite ends of the surgical thread can be returned toward the coupling portions;

wherein the opposite ends of the surgical thread can be arranged tangentially to the bone over a first stretch between the return portions inside the groove, and transversely to said bone along respective second stretches, having a greater length than the first stretch, between the return portions and the coupling portions.

2. The device according to claim 1, wherein said maneuvering member comprises:
a knob which is rotatable about the movement axis for screwing or unscrewing the screw and nut mechanism; and
a sleeve on which the two coupling portions are disposed, said knob being rotationally connected to said sleeve.

3. The device according to claim 2, wherein said elongated body and said sleeve are mutually translatable along the movement axis and rotationally fixed about the movement axis.

4. The device according to claim 1, wherein said elongated body comprises a head element comprising said tip portion and a stem extending along said longitudinal axis, said stem being operatively interposed between said head element and said maneuvering member.

5. The device according to claim 4, wherein said stem has a first end inserted into a respective recess of said maneuvering member and a second end opposite to the first end, said second end inserted into a respective recess of the head element and axially opposite said tip portion.

6. The device according to claim 5, wherein said screw and nut mechanism comprises a nut-screw fixed to the first end of the stem and a screw, the screw and nut mechanism arranged along the movement axis and fixed inside the respective recess of the maneuvering member, said screw being reversibly screwable within said nut to allow translation of said stem, wherein translation of the stem adjusts the distance between the maneuvering member and the elongated body.

7. The device according to claim 5, wherein:
said maneuvering member comprises:
a knob which is rotatable about the movement axis for screwing or unscrewing the screw and nut mechanism; and
a sleeve on which the two coupling portions are disposed, said knob being rotationally connected to said sleeve, and
said knob has an inner threaded portion and wherein said first end of the stem is threaded to be reversibly screwable inside said inner threaded portion to allow translation of said stem, wherein translation of the stem adjusts the distance between the maneuvering member and the elongated body, said first end and said inner threaded portion defining said screw and nut mechanism, respectively.

8. The device according to claim 7, comprising a spring operatively interposed between a flange of said stem and a shoulder defined by an outer edge of said head element, said spring being configured to oppose the advancement of the second end of the said stem inside the respective recess of the head element toward said tip portion.

9. The device according to claim 8, wherein said spring is arranged inside the sleeve.

10. The device according to claim 6, wherein said maneuvering member comprises an inspection eyelet through which the stem is visible, wherein said stem comprises a pin which is movable inside said inspection eyelet upon the actuation of the screw and nut mechanism, said inspection eyelet being associated with visual elements representative of the advancement of the stem.

11. The device according to claim 8, comprising a system for detecting and indicating the tension value to which the surgical thread is subjected in the use configuration of the device.

12. The device according to claim 11, wherein said head element has a window through which a portion of the stem inserted into the respective recess of the head element is visible, and wherein said detection and indication system comprises indicators obtained on said stem and on said window, said indicators representative of a tension value of the spring and/or of an insertion depth value of the stem into the recess of the head element.

13. The device according to claim 1, wherein said sidewall has two slots, each slot extending from a respective return portion toward a respective coupling portion along a respective extension direction directed toward a respective coupling portion, so that the groove and the two slots define a single "U"-shaped groove of the elongated body.

14. The device according to claim 13, wherein the extension directions of the slots are parallel to the movement axis.

15. The device according to claim 1, wherein said coupling portions comprise two jaws which are rotatable about respective parallel rotation axes, said jaws being adapted to retain said opposite ends of the surgical thread, said jaws having respective peripheral portions of increasing diameter facing each other, said peripheral portions defining a throat of variable thickness adapted to receive said opposite ends under insertion.

16. The device according to claim 15, wherein said coupling portions further comprise two torsional springs associated with the respective jaws, said torsional springs configured to progressively oppose the discordant rotation of the jaws which causes an increase in the thickness of the throat.

17. The device according to claim 15, wherein each peripheral portion has a first part having a toothed profile defining the throat and a second part having a series of retaining indents, said retaining indents disposed transversely to the rotation axes of the jaws, wherein open return and positioning recesses are disposed between the retaining indents, wherein the opposite ends of the surgical thread are interposed between said open and return positioning recesses.

18. The device according to claim 1, wherein said coupling portions comprise two bit-like elements having a through anchoring slot disposed transversely to the movement direction.

19. The device according to claim 1, wherein said tip portion has a secondary groove extending transversely to the groove and shaped to at least partially receive said knot at a point of intersection with said groove, wherein said secondary groove extends perpendicularly to the movement axis and opens on opposite sides of the sidewall of said elongated body at two openings, wherein the openings allow for the passage of the surgical thread part wound about the bone.

20. A bone cerclage kit comprising:
   a surgical thread made of a biocompatible fabric configured to be wound about a patient's bone to obtain a knot, and
   a device for tensioning said surgical thread according to claim 1;
      wherein said groove of the tip portion is configured to contact said knot in the use configuration of the device.

* * * * *